(12) United States Patent
Ma et al.

(10) Patent No.: US 11,255,556 B1
(45) Date of Patent: Feb. 22, 2022

(54) DISINFECTING DEVICE FOR CENTRAL AIR CONDITIONER

(71) Applicant: HUAZHONG UNIVERSITY OF SCIENCE AND TECHNOLOGY, Hubei (CN)

(72) Inventors: Xiuquan Ma, Hubei (CN); Shaowei Zhou, Hubei (CN); Qing Liu, Hubei (CN); Tianyu Xu, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 17/404,685

(22) Filed: Aug. 17, 2021

(30) Foreign Application Priority Data

Aug. 18, 2020 (CN) .......................... 202010828661.9

(51) Int. Cl.
*F24F 8/22* (2021.01)
*A61L 9/20* (2006.01)

(52) U.S. Cl.
CPC .................. *F24F 8/22* (2021.01); *A61L 9/20* (2013.01); *A61L 2209/12* (2013.01)

(58) Field of Classification Search
CPC ........... A61L 9/20; A61L 2209/12; F24F 8/22
See application file for complete search history.

(56) References Cited

U.S. PATENT DOCUMENTS

2017/0080373 A1\* 3/2017 Engelhard ............ B01D 46/442

FOREIGN PATENT DOCUMENTS

| CN | 205698628 U | 11/2016 |
| CN | 111256249 A | 6/2020 |
| CN | 111895541 B | 5/2021 |

OTHER PUBLICATIONS

Applicant: Huazhong University of Science and Technology; Chinese Application No. 202010828661.9; First Chinese Office Action; 12 pgs.
Applicant: Huazhong University of Science and Technology; "Disinfection and sterilization device for central air conditioner"; Chinese Application No. 202010828661.9; Notification to Grant Patent Right for Invention; 3 pgs.

\* cited by examiner

*Primary Examiner* — Sean E Conley

(74) *Attorney, Agent, or Firm* — Tarolli, Sundheim, Covell & Tummino LLP

(57) ABSTRACT

The present disclosure provides a disinfecting device for a central air conditioner, which uses high-powered ultraviolet rays to efficiently and rapidly eliminate viruses, and uses two sets of parallel reflectors to reflect and overlap light curtains of the high-powered ultraviolet rays back and forth. In this way, small-sized aerosols with viruses can be eliminated, and no secondary pollutants such as ozone are produced in a process of purifying and disinfecting air by the ultraviolet rays. The entire device has a simple structure and can be used in the central air conditioner with an existing architecture. The entire device only needs to be provided in an air supply duct of the central air conditioner.

4 Claims, 2 Drawing Sheets

DISINFECTING DEVICE FOR CENTRAL AIR CONDITIONER

CROSS-REFERENCE TO RELATED APPLICATION

This patent application claims the benefit and priority of Chinese Patent Application No. 202010828661.9, filed on Aug. 18, 2020, the disclosure of which is incorporated by reference herein in its entirety as part of the present application.

TECHNICAL FIELD

The present disclosure relates to the technical field of air purification, and in particular, to a disinfecting device for a central air conditioner.

BACKGROUND ART

Dust in a central air-conditioning system can serve as media for viruses and bacteria to spread pathogens to rooms with people, causing epidemic of respiratory infectious diseases via airborne transmission. In addition, particulate matters in ventilation ducts, microbial aerosols produced by cooling towers and humidifiers, dust mites deposited on a surface of air filters, and the like are also very likely to spread in crowded office buildings, endangering the health of people.

Conventional indoor disinfection methods are performed by using disinfectant, ultraviolet lamps, air purifiers, and the like. In the disinfecting device for the central air conditioner, a plasma photocatalytic method using nanomaterials is often used. The principle is to dispose a nanomaterial of titanium dioxide ($TiO_2$) on an electrode plate of the purification device to form a titanium dioxide film with a high specific surface area and high oxidability. Ultraviolet rays with a wavelength (350 to 400 nm) emitted when the plasma is discharged under a low temperature are used to generate active substances with high performance, and the active substances are combined with the hydroxyl radicals of the plasma, causing a composite catalytic oxidation effect. The device has a complex structure and a better function of removing large suspended particles in the air, but it cannot effectively extinguish the extremely tiny suspended particles with viruses in the air, for example, aerosols. In addition, the entire device is very complex and needs professional maintenance, and its functions of air purification and disinfection will also fade away with time.

Currently, common indoor disinfection devices are the ultraviolet lamps and the air purifiers. The ultraviolet lamps eliminate viruses by using ultraviolet rays emitted by mercury lamps. The ultraviolet rays emitted by mercury lamps contain a larger amount of power, and if no protective measures are taken, great harms are likely to be caused to the human body. In addition, the ultraviolet lamps will also generate ozone, causing secondary pollution. Therefore, the ultraviolet lamps are often used at night with no humans around, and cannot work uninterruptedly around the clock. Currently, purification technologies using plasmas and powerful filters are usually applied to the air purifiers with disinfection functions on the market. This method is only suitable for a condition with large suspended particles in the air, and the purification efficiency is low. In large crowded offices, air purification and disinfection effects are poor, and therefore, the method is not suitable for the central air conditioner.

An effective disinfection device applicable to the central air conditioner urgently needs to be provided.

SUMMARY

The present disclosure is intended to provide a disinfecting device for a central air conditioner, to effectively disinfect the central air conditioner.

To implement the above objectives, the present disclosure provides the following solutions:

A disinfecting device for a central air conditioner is provided, including an ultraviolet laser, two reflectors, and an air duct cavity;

the air duct cavity is provided in an air supply duct of the central air conditioner;

the ultraviolet laser is provided outside the air duct cavity, and the two reflectors are respectively provided on an upper wall and a lower wall inside the air duct cavity; and the ultraviolet laser is configured to emit ultraviolet rays with an incident angle of β, and the ultraviolet rays are emitted to the reflector on the lower wall inside the air duct cavity through an ultraviolet ray inlet provided on the air duct cavity, are reflected by the two reflectors for multiple times to disinfect airflow flowing through the air duct cavity, and are emitted out through an ultraviolet ray outlet provided on the air duct cavity.

Optionally, the disinfecting device further includes an ultraviolet ray absorber, the ultraviolet ray absorber is provided at the ultraviolet ray outlet, and the ultraviolet ray absorber is configured to convert into thermal power the ultraviolet rays emitted from the ultraviolet ray outlet, and release the thermal power.

Optionally, a water cooling mechanism and/or an air cooling mechanism are/is provided in the ultraviolet ray absorber.

Optionally, a concave mirror is also provided in the ultraviolet ray absorber, and the concave mirror is configured to disperse the ultraviolet rays emitted from the ultraviolet ray outlet.

Optionally, the disinfecting device also includes two reflector-specific cooling fins; and the two reflector-specific cooling fins are respectively provided on the upper wall and the lower wall inside the air duct cavity, and the two reflectors are respectively provided on the two reflector-specific cooling fins.

Optionally, an optical component is provided in the ultraviolet laser, and the optical component is configured to shape the ultraviolet rays emitted by the ultraviolet laser.

Optionally, the incident angle β of the ultraviolet rays can be adjusted, and the incident angle β of the ultraviolet rays is adjusted to adjust the number of reflections of the ultraviolet rays between the two reflectors.

Based on specific embodiments provided in the present disclosure, the present disclosure discloses the following technical effects:

The present disclosure discloses the disinfecting device for the central air conditioner, to use the high-powered ultraviolet rays to efficiently and rapidly eliminate viruses, and use two sets of parallel reflectors to reflect and overlap light curtains of the high-powered ultraviolet rays back and forth. In this way, small-sized aerosols with viruses can be eliminated, and no secondary pollutants such as ozone are produced in a process of purifying and disinfecting the air by the ultraviolet rays. The entire device has a simple structure and can be used in the central air conditioner with the existing architecture. The entire device only needs to be provided in an air supply duct of the central air conditioner.

In the present disclosure, the incident angle of the ultraviolet rays is also adjusted, to increase the number of reflections for efficient disinfection.

BRIEF DESCRIPTION OF THE DRAWINGS

To describe the technical solutions in the embodiments of the present disclosure or in the prior art more clearly, the accompanying drawings required for the embodiments are briefly described below. Apparently, the accompanying drawings in the following description show merely some embodiments of the present disclosure, and a person of ordinary skill in the art may still derive other accompanying drawings from these accompanying drawings without creative efforts.

DETAILED DESCRIPTION OF THE EMBODIMENTS

The present disclosure is intended to provide a disinfecting device for a central air conditioner, to provide an effective disinfection device applicable to the central air conditioner.

To make the foregoing objective, features, and advantages of the present disclosure clearer and more comprehensible, the present disclosure is further described in detail below with reference to the accompanying drawings and specific examples.

Figure 1:
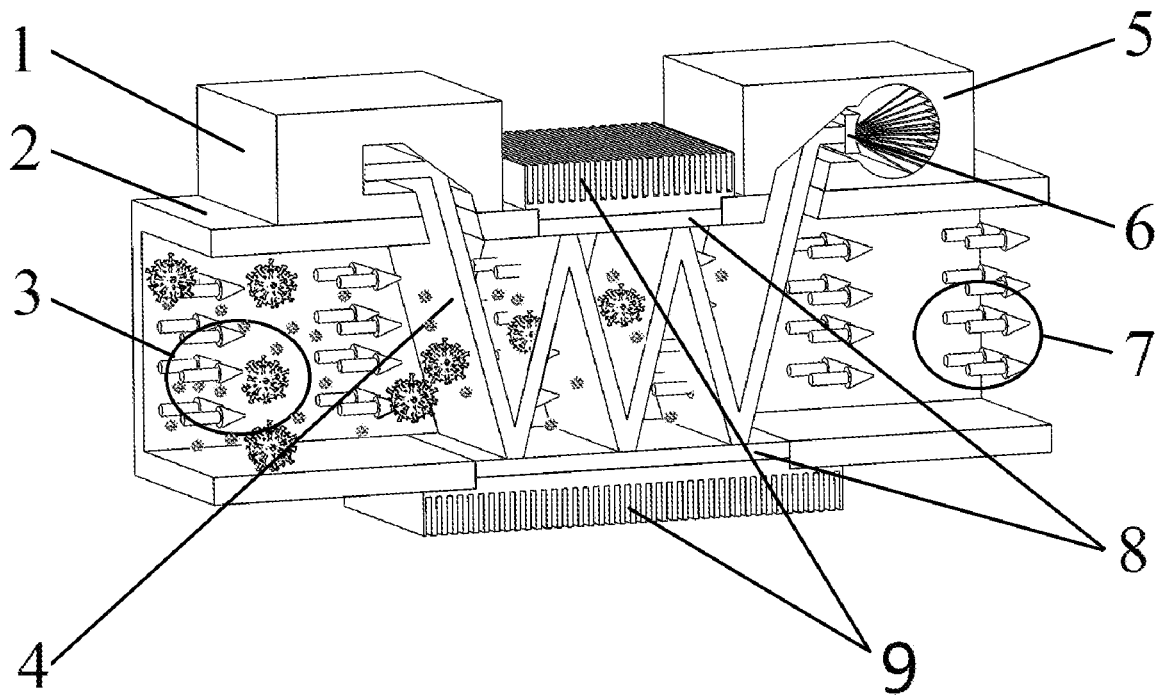
FIG. 1 is a cross-sectional view of a disinfecting device for a central air conditioner according to the present disclosure.
Figure 2:
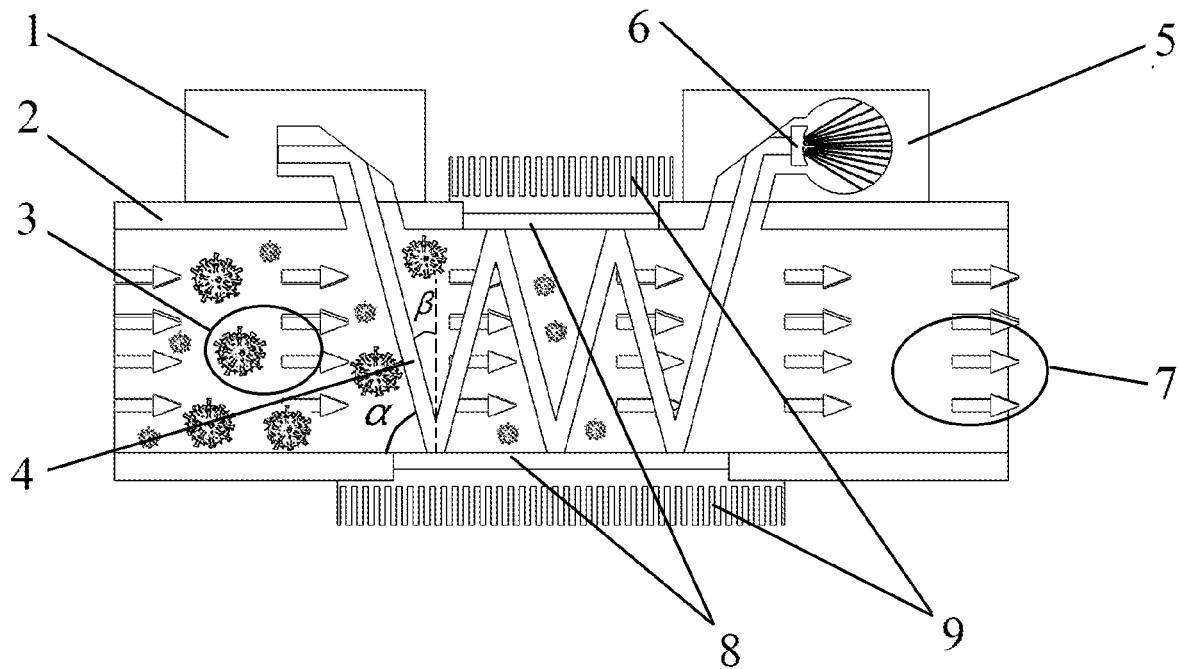
FIG. 2 is a front view of a disinfecting device for a central air conditioner according to the present disclosure.
Figure 3:
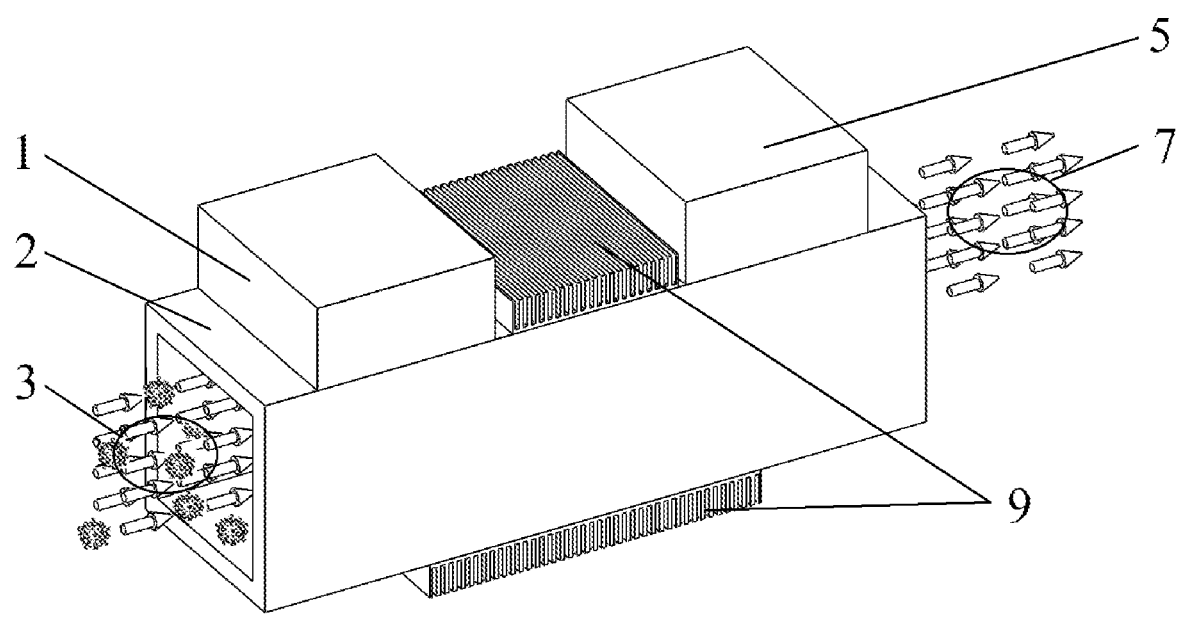
FIG. 3 is a three-dimensional diagram of a disinfecting device for a central air conditioner according to the present disclosure.

As shown in FIG. 1 to FIG. 3, the present disclosure provides a disinfecting device for a central air conditioner, including: an ultraviolet laser 1, an air duct cavity 2, reflectors 8, an ultraviolet ray absorber 5, a rectangular concave mirror provided inside ultraviolet ray absorber 5, and reflector-specific cooling fins 9 provided with the reflectors 8.

The ultraviolet laser 1 is a laser that generates an ultraviolet beam; and a power density is tens of millions of times higher than that of a common ultraviolet lamp. The ultraviolet rays generated by the ultraviolet laser are shaped by an internal optical component, and has a rectangular cross-section.

The air duct cavity 2 is provided in an air supply duct of the central air conditioner.

Turbid air 3 contains viruses and bacteria.

The shaped ultraviolet rays 4 are generated by the ultraviolet laser 1 and emitted to the reflectors 8. As shown in FIG. 2, an incident angle is $\beta$, and an angle between the reflector 8 and the ultraviolet rays is $\alpha$, where $\alpha+\beta=90°$. Adjusting the incident angle $\beta$ can control the number of reflections on the reflectors 8 with a fixed length, thereby increasing time of contact between the ultraviolet rays and the air.

The ultraviolet ray absorber 5 is configured to convert the power of the ultraviolet rays into heat, which is cooled by an internal water cooling or air cooling mechanism.

The rectangular concave mirror 6 is configured to diverge parallel ultraviolet rays to reduce the power density of the ultraviolet rays, and the rectangular concave mirror 6 is provided inside the ultraviolet ray absorber 5.

Pure air 7 is disinfected by the ultraviolet rays, and pollutants such as aerosols with viruses, and bacteria in the turbid air 3 are eliminated.

There are two parallel reflectors 8. The shaped ultraviolet rays 4 are emitted to two reflectors, reflected back and forth, and finally emitted to the ultraviolet ray absorber 5.

The reflectors 8 are closely attached to the reflector-specific cooling fins 9 to dissipate heat for the reflectors.

Technical effects of the present disclosure are as follows:

1. The ultraviolet laser is proposed to replace the conventional ultraviolet laser lamp. In the method, a structure is simple, and secondary pollutants such as ozone are not produced. Since the power of ultraviolet laser is tens of millions of times larger than that of the conventional ultraviolet lamp, pollutants such as viruses can be eliminated instantly. Therefore, the disinfection effect is excellent.

2. The two sets of reflectors are configured to reflect the ultraviolet rays back and forth, to increase the time of reaction between the turbid air and the ultraviolet rays and eliminate the pollutants in the air level by level, further improving the disinfection efficiency. Adjusting the incident angle $\beta$ of the ultraviolet rays can adjust the number of reflections 3. The structures such as filters are omitted in the device, and the air duct is hardly affected, and no air resistance is caused, reducing power consumption of the central air conditioner, and reducing the use costs.

4. The device uses the ultraviolet ray absorber to convert excess ultraviolet rays into heat, dissipates the heat by using the air cooling device or the water cooling device, and has a simple structure.

Compared with the existing ultraviolet lamp, the power of ultraviolet laser is tens of millions of times higher than that of the ultraviolet lamp, and during the reaction between the ultraviolet rays and the air, secondary pollutants such as ozone are not produced. The directivity of ultraviolet rays is excellent. The ultraviolet rays are finally completely absorbed by the absorber inside the device, and there is no leakage to cause harms to the human body. Therefore, the device can work uninterruptedly around the clock.

Compared with the air purifier with virus elimination functions, the device has a simple structure, can eliminate extremely tiny bacteria and viruses in the air, has high purification efficiency, and does not have a filter or other equipment that needs to be cleaned and replaced later, and therefore, maintenance costs are low.

Compared with the air purification device used for the central air conditioner, the device does not have complicated catalytic equipment. Two sets of parallel reflectors are used to reflect and overlap the light curtain of the ultraviolet rays back and forth, to increase the time of reaction between the polluted air and the ultraviolet rays. In the method, the small-sized aerosols with viruses can be eliminated. The incident angle of the ultraviolet laser is adjusted to increase the number of reflections for efficient elimination. In addition, the original air duct structure of the central air conditioner is not changed to add the device, air resistance is not additionally increased, and the power consumption of the air conditioner is hardly increased. The device can work uninterruptedly around the clock and does not produce the secondary pollutants such as ozone. The entire device has a simple structure and can be used in the central air conditioner with the existing architecture. The entire device only needs to be provided in an air supply duct of the central air conditioner. The virus elimination capability of the device hardly fades away with time.

Each example of the present specification is described in a progressive manner, each example focuses on the difference from other examples, and the same and similar parts between the examples may refer to each other.

The principles and implementations of the disclosure have been described with reference to specific examples. The description of the above examples is only for facilitating understanding of the method and the core idea of the disclosure, and the described examples are only a part of the examples of the disclosure. All other examples obtained by a person of ordinary skill in the art based on the examples of the disclosure without departing from the inventive scope are the scope of the disclosure.

What is claimed is:

1. A disinfecting device for a central air conditioner, wherein the disinfecting device comprises: an ultraviolet laser, two reflectors, and an air duct cavity;
   the air duct cavity is provided in an air supply duct of the central air conditioner;
   the ultraviolet laser is provided outside the air duct cavity, and the two reflectors are respectively provided on an upper wall and a lower wall inside the air duct cavity;
   the ultraviolet laser is configured to emit ultraviolet rays with an incident angle of β, and the ultraviolet rays are emitted to the reflector on the lower wall inside the air duct cavity through an ultraviolet ray inlet provided on the air duct cavity, are reflected by the two reflectors for multiple times to disinfect airflow flowing through the air duct cavity, and are emitted out through an ultraviolet ray outlet provided on the air duct cavity;
   the disinfecting device further comprises an ultraviolet ray absorber, the ultraviolet ray absorber is provided at the ultraviolet ray outlet, and the ultraviolet ray absorber is configured to convert into thermal power the ultraviolet rays emitted from the ultraviolet ray outlet, and release the thermal power;
   water cooling mechanism and/or an air cooling mechanism are/is provided in the ultraviolet ray absorber; and
   a concave mirror is further provided in the ultraviolet ray absorber, and the concave mirror is configured to disperse the ultraviolet rays emitted from the ultraviolet ray outlet.

2. The disinfecting device for a central air conditioner according to claim 1, wherein the disinfecting device further comprises two reflector-specific cooling fins; and
   the two reflector-specific cooling fins are respectively provided on the upper wall and the lower wall inside the air duct cavity, and the two reflectors are respectively provided on the two reflector-specific cooling fins.

3. The disinfecting device for a central air conditioner according to claim 1, wherein an optical component is provided in the ultraviolet laser, and the optical component is configured to shape the ultraviolet rays emitted by the ultraviolet laser.

4. The disinfecting device for a central air conditioner according to claim 1, wherein the incident angle β of the ultraviolet rays can be adjusted, and the incident angle β of the ultraviolet rays is adjusted to adjust the number of reflections of the ultraviolet rays between the two reflectors.

* * * * *